United States Patent
Hong et al.

(10) Patent No.: US 11,952,575 B2
(45) Date of Patent: Apr. 9, 2024

(54) TRANSAMINASE MUTANT AND USE THEREOF

(71) Applicant: Asymchem Life Science (Tianjin) Co., Ltd, Tianjin (CN)

(72) Inventors: Hao Hong, Tianjin (CN); Gage James, Tianjin (CN); Jiangping Lu, Tianjin (CN); Xingfu Xu, Tianjin (CN); Wenyan Yu, Tianjin (CN); Xin Huang, Tianjin (CN); Yulei Ma, Tianjin (CN); Yibing Cheng, Tianjin (CN)

(73) Assignee: ASYMCHEM LIFE SCIENCE (TIANJIN) CO., LTD, Tianjin (CN)

( * ) Notice: Subject to any disclaimer, the term of this patent is extended or adjusted under 35 U.S.C. 154(b) by 1046 days.

(21) Appl. No.: 16/652,291

(22) PCT Filed: Nov. 15, 2017

(86) PCT No.: PCT/CN2017/111161
§ 371 (c)(1),
(2) Date: Mar. 30, 2020

(87) PCT Pub. No.: WO2019/095161
PCT Pub. Date: May 23, 2019

(65) Prior Publication Data
US 2020/0239895 A1   Jul. 30, 2020

(51) Int. Cl.
*C12N 9/00* (2006.01)
*C12N 15/70* (2006.01)
*C12P 13/00* (2006.01)

(52) U.S. Cl.
CPC ............ *C12N 15/70* (2013.01); *C12P 13/001* (2013.01); *C12Y 206/01* (2013.01)

(58) Field of Classification Search
CPC .... C12N 9/1096; C12N 15/70; C12N 15/102; C12N 15/1034; C12N 15/63; C12P 13/001; C12P 41/006
USPC ....................................................... 435/189
See application file for complete search history.

(56) References Cited

FOREIGN PATENT DOCUMENTS

| CN | 103827309 A | 5/2014 |
| CN | 107034247 A | 8/2017 |

OTHER PUBLICATIONS

Kisselev L., (Structure, 2002, vol. 10: 8-9.*
Witkowski et al., (Biochemistry 38:11643-11650, 1999.*
Whisstock et al., (Quarterly Reviews of Biophysics 2003, vol. 36 (3): 307-340.*
Devos et al., (Proteins: Structure, Function and Genetics, 2000, vol. 41: 98-107.*
Extended European Search Report issued for EP 21 19 3067, dated Feb. 23, 2022 (7 pages).
Manta, B. et al.; "Quantum Chemical Study of Dual-Substrate Recognition in [omega]-Transaminase"; ACS Omega, 2017, vol. 2, pp. 890-898 (9 sheets).
Du, C.; "Bioconversion of lignin degradation products into value-added chemicals"; Retrieved from Internet: URL: https://ethos.bl.uk/OrderDetails.do?uin=uk.bl.ethos.626524, retrieved Jan. 1, 2021.
Japanese Office Action issued for JP 2020-515724, dated Aug. 26, 2021.
Japanese Office Action issued for JP 2020-515724, dated Mar. 25, 2021.
Nakahigashi, K. et al.; "Hemk, a class of protein methyl transferase with similiarity to DNA methyl transferases, methylates polypeptide chain release factors, and hemK knockout induces defects in translational termination"; PNAS, vol. 99, No. 3, Feb. 5, 2002, pp. 1473-1478 (6 sheets).
International Search Report issued for PCT/CN2017/111161, dated Aug. 17, 2018.
Deszcz, D. et al.; "Single Active-Site Mutants are Sufficient to Enhance Serine: Pyruvate A-Transaminase Activity in an X-Transaminase"; The FEBS Journal, vol. 282, No. (13), Apr. 6, 2015, pp. 2512-2526.
Westlake, A.C.; "Crystallisation and Structural Studies on Omega Transaminase Enzymes"; Open Research Exeter (ORE), Mar. 9, 2012, pp. 1-71.
"UniProtKB/TrEMBL registry No. Q7NWG4"; UniProtKB/TrEMBL Database, Dec. 15, 2003 (6 pages).

* cited by examiner

*Primary Examiner* — Robert B Mondesi
*Assistant Examiner* — Mohammad Y Meah
(74) *Attorney, Agent, or Firm* — ArentFox Schiff LLP

(57) ABSTRACT

A transaminase mutant and use hereof, the amino acid sequence of the transaminase mutant is an amino acid sequence in which the amino acid sequence as represented by SEQ ID NO: 1 is mutated, the mutated amino acid position being one or more selected from among F89, K193, P243, V234, I262, Q280, V379, R416, A417 and C418. The enzymatic activity and/or stability of the transaminase mutant is improved.

6 Claims, No Drawings
Specification includes a Sequence Listing.

TRANSAMINASE MUTANT AND USE THEREOF

CROSS-REFERENCE TO RELATED APPLICATION

This application is the U.S. National Stage Application of International Patent Application No. PCT/CN2017/111161, filed Nov. 15, 2017, the content of which is incorporated by reference in its entirety herein.

SEQUENCE LISTING

The instant application contains a Sequence Listing which has been submitted electronically in ASCII format and is hereby incorporated by reference in its entirety. Said ASCII copy is named PN125557 Sequence Listing.txt and is 10.4 kilobytes in size.

TECHNICAL FIELD

The disclosure relates to the field of enzyme engineering, and in particular, to a transaminase mutant and use thereof.

BACKGROUND

Enzymes, as biocatalysts, may give full play to high efficiency and high specificity characters thereof in vivo. However, in industrial applications, there are generally problems, such as inability to adapt to industrial production conditions and low catalytic ability to non-natural substrates. Site-directed mutagenesis and saturation mutation technologies are effective means to modify enzyme molecules.

The site-directed mutagenesis (or site-specific mutagenesis) refers to a method of introducing a specific base pair at a designated site of a DNA fragment of interest. Changing an encoded amino acid sequence by changing a nucleotide sequence of a specific site of a gene is often used to study the effect of a certain amino acid residue(s) on the structure and function of a protein. In a rational design of the enzymes, a site-directed mutagenesis method may be used for screening mutant enzymes with improved catalytic activity, substrate specificity, and/or stability.

Saturation mutation is a method to obtain a mutant in which an amino acid in a target side is replaced by 19 other amino acids, respectively, by modifying the coding gene of the protein of interest in a short time. This method is not only a powerful tool for protein orientation modification, but also an important means for studying the structure-function relationship of proteins. The saturation mutation may often acquire a more ideal evolution than single-point mutations. These problems which the site-directed mutagenesis method may not solve are exactly the uniqueness of the saturation mutation method.

An ω-transaminase (ω-TA) belongs to the class of transferase, and, like other transaminases, catalyzes a process of exchange between an amino group and a keto group. The ω-transaminase uses a ketone compound as a raw material, and through stereoselective transamination, may efficiently produce chiral amines, and has attracted the attention of many researchers.

3-aminopyrrolidine derivatives and optical isomers thereof are a chiral amine compound, and is a key intermediate for synthesizing a large number of chiral drugs or agricultural chemicals. (S)-1-benzyloxycarbonyl-3-aminopyrrolidine is an important 3-aminopyrrolidine derivative with optical activity. It is reported by J. M. C 1992, 35, 1764 that (S)-1-benzyloxycarbonyl-3-aminopyrrolidine is prepared using (R)-1-benzyl-3-pyrrolidinol as a starting raw material in a five-step reaction, an ee value thereof is 96%, and the synthetic route is as follows:

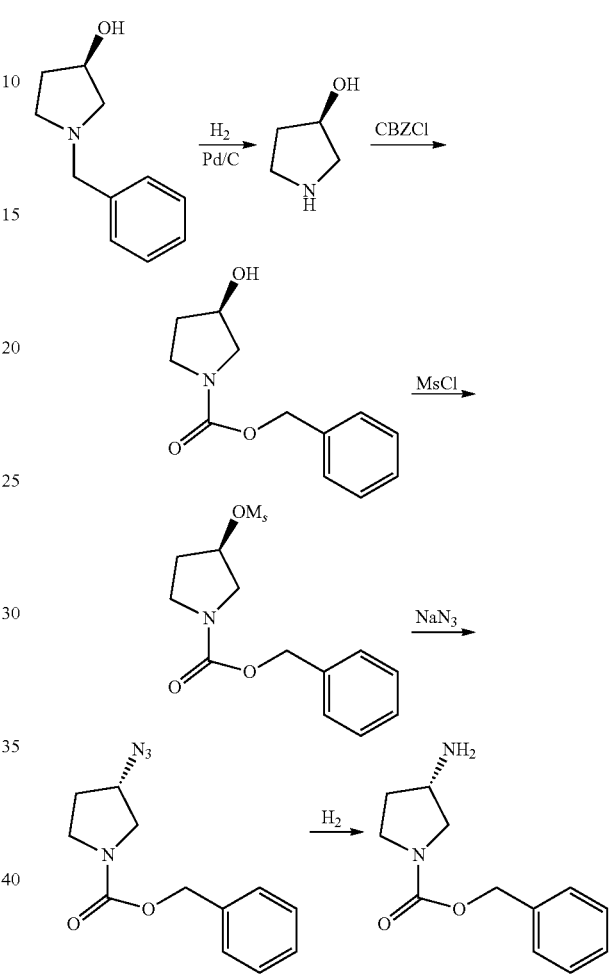

The starting raw material of this synthetic route is high in price, and a harmful reagent sodium azide is used in the synthetic process, requirements to operation equipment, personnel safety, three-waste treatment and the like are higher, and pollution to the environment is greater. However, there are few reports on asymmetric synthesis of chiral (S)-1-benzyloxycarbonyl-3-aminopyrrolidine using bioenzyme biocatalysis at present.

Although it has also been reported that the transaminase may be used as a biocatalyst to reduce a ketone substrate in one-step, to prepare the (S)-1-benzyloxycarbonyl-3-aminopyrrolidine with high optical purity. Compared with a traditional chemical method, a biological transformation method is mild in reaction condition, and avoids using strong oxidants, strong reducing agents and dangerous reagents. The conditions are mild, and the pollution to the environment is low.

However, in applications of the biological transformation method in industrial production, there are still some problems which need to be further solved. In this method, the enzyme catalytic activity is not efficient enough, a total volume of a reaction system thereof is 40-60 ml/g substrate, and the reaction system has a large volume, which leads to an increase in production batches and production cost, and a large amount of organic solvents in a post-treatment process, the difficulty of reaction post-treatment may be increased, and a larger burden may be brought to the environment. In addition, in the prior art, D-alanine or L-alanine or a salt thereof is mostly used as an amino donor, and coupling coenzyme systems, such as glucose and GDH, ammonium formate and FDH, also need to be added to the reaction system.

Therefore, the biological transformation methods in the prior art still needs to be improved, as to improve the catalytic characteristics of the transaminase, reduce the total volume of the reaction system, reduce the production cost, and reduce the environment pollution.

SUMMARY

The disclosure aims to provide a transaminase mutant and an application thereof, as to improve catalytic activity thereof.

In order to achieve the above objective, according to one aspect of the present application, a transaminase mutant is provided, an amino acid sequence of the transaminase mutant is a mutated amino acid sequence of SEQ ID NO: 1, and one or more of mutated amino acid sites are selected from a group consisting of F89, K193, P243, V234, I262, Q280, V379, R416, A417 and C418.

Further, one or more of the mutated amino acid sites are selected from a group consisting of P243E, F89Y/W, K193E, V234I, I262V, Q280K, V379L/M/T, R416A/C/H/Q/T/S, A417S and C418A/Q/S, wherein "/" stands for "or".

Further, the mutated amino acid sites comprises any one of the following combinations: V379L/M/T+F89Y/W, V379L/M/T+R416A/C/H/Q/T/S, V379L/M/T+A417S, V379L/M/T+C418A/Q/S, V379L/M/T+P243E, V379L/M/T+K193E, V379L/M/T+V234I, V379L/M/T+I262V, V379L/M/T+Q280K, R416A/C/H/Q/T/S+A417S, R416A/C/H/Q/T/S+C418A/Q/S, R416A/C/H/Q/T/S+F89Y/W, R416A/C/H/Q/T/S+A417S+F89Y/W, V379L/M/T+R416A/C/H/Q/T/S+F89Y/W, V379L/M/T+R416A/C/H/Q/T/S+A417S, V379L/M/T+R416A/C/H/Q/T/S+C418A/Q/S, V379L/M/T+R416A/C/H/Q/T/S+K193E, V379L/M/T+R416A/C/H/Q/T/S+V234I, V379L/M/T+C418A/Q/S+F89Y/W, V379L/M/T+C418A/Q/S+P243E, V379L/M/T+C418A/Q/S+I262V, V379L/M/T+A417S+Q280K, V379L/M/T+R416A/C/H/Q/T/S+C418A/Q/S+F89Y/W, V379L/M/T+R416A/C/H/Q/T/S+C418A/Q/S+Q280K, V379L/M/T+R416A/C/H/Q/T/S+C418A/Q/S+F89Y/W+Q280K, V379L/M/T+R416A/C/H/Q/T/S+C418A/Q/S+F89Y/W+Q280K+I262V, V379L/M/T+R416A/C/H/Q/T/S+C418A/Q/S+F89Y/W+Q280K+A417S and V379L/M/T+R416A/C/H/Q/T/S+C418A/Q/S+F89Y/W+Q280K+I262V+V234I.

In order to achieve the above objective, according to a second aspect of the present application, a DNA molecule is provided, the DNA molecule encodes any one of the transaminase mutants.

According to a third aspect of the present application, a recombinant vector is provided, the DNA molecule is effectively linked with the recombinant vector.

Further, the recombinant vector is selected from a group consisting of pET-21b (+), pET-22b(+), pET-3a(+), pET-3d (+), pET-11a(+), pET-12a(+), pET-14b (+), pET-15b(+), pET-16b(+), pET-17b(+), pET-19b(+), pET-20b(+), pET-21a (+), pET-23a(+), pET-23b(+), pET-24a(+), pET-25b(+), pET-26b(+), pET-27b (+), pET-28a(+), pET-29a(+), pET-30a (+), pET-31b(+), pET-32a(+), pET-35b (+), pET-38b(+), pET-39b(+), pET-40b(+), pET-41a(+), pET-41b(+), pET-42a (+), pET-43a(+), pET-43b(+), pET-44a(+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pBV220, pBV221, pBV222, pTrc99A, pTwin1, pEZZ18, pKK232-18, pUC-18 or pUC-19.

According to a fourth aspect of the present application, a host cell is provided. The host cell contains any one of the above recombinant vectors.

Further, the host cell is a prokaryotic cell or a eukaryocyte cell; preferably, the prokaryotic cell is a yeast cell; preferably, the host cell is a competent cell, further preferably, the competent cell is an *E. coli* BL21 cell or an *E. coli* W3110.

According to a fourth aspect of the disclosure, a method for synthesizing a chiral amine is provided. The method includes a step of performing a catalytic transamination reaction on a ketone compound and an amino donor with a transaminase, herein the transaminase is any one of the above transaminase mutants.

Further, the ketone compound is

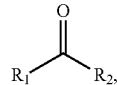

herein, each of R1 and R2 is independently a C1-C8 alkyl, a C5-C10 cycloalkyl, a C5-C10 aryl or a C6-C10 heteroaryl, or the R1 and the R2 jointly form a C5-C10 heterocyclyl, a C5-C10 carbocyclyl or the C5-C10 heteroaryl with carbon in a carbonyl, one or more of heteroatoms in the C5-C10 heterocyclyl and the C5-C10 heteroaryl are independently selected from at least one of nitrogen, oxygen and sulfur, and each of an aryl in the C6-C10 aryl, a heteroaryl in the C5-C10 heteroaryl, a carbocyclyl in the C5-C10 carbocyclyl or a heterocyclyl in the C5-C10 heterocyclyl is independently unsubstituted or substituted by at least one group of halogen, an alkoxy or an alkyl, preferably, the ketone compound is

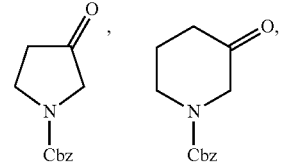 [SMILES: O=C1CCN(C(=O)OCc2ccccc2)C1 ; O=C1CCCN(C(=O)OCc2ccccc2)C1]

a product of the transaminase reaction is

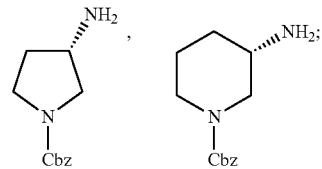 [SMILES: N[C@H]1CCN(C(=O)OCc2ccccc2)C1 ; N[C@H]1CCCN(C(=O)OCc2ccccc2)C1]

preferably, the amino donor is isopropylamine or an isopropyl amine salt.

By applying the technical scheme of the disclosure, the ω-transaminase is improved using the site-directed mutagenesis and/or saturation mutation method, and the ω-transaminase mutants with high catalytic efficiency and/or high stability is obtained. Based on partial ω-transaminase mutants obtained in the present application, in synthesis of a (S)-1-benzyloxycarbonyl-3-aminoheterocycle compound (especially (S)-1-benzyloxycarbonyl-3-aminopyrrolidine and (S)-1-benzyloxycarbonyl-3-aminopiperidine), the amount e of the enzyme is reduced to 0.3-0.5 wt, the reaction volume is reduced to 10-20 V, a utilization ratio of the enzyme and a utilization ratio of a reaction kettle are greatly improved, the production batches of the enzyme solution and a usage amount of a material are reduced, and a usage amount of the organic solvent in the post-treatment is effectively reduced, so the difficulty of the post-treatment and a discharge amount of three wastes are reduced, and the labor cost is reduced. In addition, through the obtained (S)-1-benzyloxycarbonyl-3-aminopyrrolidine and (S)-1-benzyloxycarbonyl-3-aminopiperidine with high optical purity, the industrial production cost of the compound is greatly reduced, and the enzyme has a better application value in industrial production.

DETAILED DESCRIPTION OF THE EMBODIMENTS

It is to be noted that embodiments in the present application and features in the embodiments may be mutually combined in the case without conflicting. The disclosure is described in detail below in combination with the embodiments.

Term Explanation:

Catalytic activity: refers to an amount of a raw material reactant transformed per unit volume (or mass) of a catalyst in a unit time. In the disclosure, a level of the catalytic activity of a transaminase is positively related to a transformation rate of the reaction raw material in the disclosure.

Evolution: means of mutation or recombination and the like are used to create molecular diversity, and then screen the diversity, as to obtain a gene or DNA with a new function. In the disclosure, a wild-type transaminase is modified by means of mutation or recombination and the like, as to obtain the transaminase with improved performance.

Wild-type: refers to those obtained from nature, without artificial mutagenesis or modified. In the disclosure, the wild-type ω-transaminase refers to a natural transaminase encoded by a gene sequence which is not artificially modified and obtained by screening from Genebank.

Immobilized enzyme: refers to an enzyme whose catalytic function can be used repeatedly and continuously in a certain space range. Generally, an enzyme-catalyzed reaction is performed in an aqueous solution, and the immobilized enzyme is a water-soluble enzyme which is physically or chemically treated to make it insoluble in water, but still has enzyme activity. After the enzyme is immobilized, the stability is increased generally, it is easy to separate from a reaction system and easy to control, it may be used for multiple times, it is convenient for transporting and storing, and beneficial to automatic production, but the activity is reduced, and the usage range is reduced.

Immobilized cell: is a method used to obtain enzymes and metabolites of a cell, and developed on the basis of the immobilized enzyme. The immobilized cell refers to a cell which is immobilized on an insoluble carrier and performs life activity in a certain space range. Because the immobilized cell may perform normal growth, reproduction and metabolism, the immobilized cell is also called an immobilized viable cell or an immobilized proliferative cell.

In the disclosure, the related 1 wt refers to 1 g of transaminase mutant recombinant wet cells required to transform 1 g of a main raw material.

In the disclosure, the related 1 V is equal to a volume of a reaction system/a mass of a substrate.

The site-directed mutagenesis and/or saturation mutation method is used for transforming the transaminase, as to improve the catalytic activity thereof, substrate specificity and/or stability, it is helpful to solve problems existing in an prior art, such as a dosage of enzyme solution is larger, a reaction system is large, and production cost is high. A main objective of the disclosure is to improve an ω-transaminase by using an enzyme molecule transformation method to obtain an ω-transaminase mutant with high catalytic efficiency and/or high stability, as to solve the deficiency in the prior art, and improve an application value of industrial production thereof.

In the disclosure, a wild-type ω-transaminase gene derived from *Chromobacterium violaceum* is used as a starting gene, because the transaminase (having the amino acid sequence as shown in SEQ ID NO: 1) encoded by the wild-type gene has relatively higher activity itself, 3 wt of wild-type transaminase bacterial sludge is used, and a reaction may be basically transformed and completed. Based on the wild-type transaminase with relatively higher catalytic activity, it is difficult to obtain a transaminase with further improved catalytic activity through evolution transformation of an enzyme molecule. Therefore, the disclosure performs the site-directed mutagenesis in 36 sites, and 1500 mutant strains are screened by the saturation mutation, so that the following ω-transaminase mutants with improved catalytic activity and/or stability are obtained.

An amino acid site of a mutation capable of improving the catalytic activity and/or the stability of the ω-transaminase mutant is selected from one or more of F89, K193, P243, V234, I262, Q280, V379, R416, A417 and C418. Herein, a site capable of improving the catalytic activity is selected from: F89, K193, P243, V234, I262, Q280, V379, R416, A417 and C418, these sites are positioned near an enzyme catalytic center, and may be related to substrate entry or binding.

The above transaminase is obtained, through selecting SEQ ID NO: 1 as a basic sequence, and genetically engineered to obtain a mutation containing one or more amino acid residues changes, and the catalytic activity and/or stability thereof is remarkably improved.

On the basis of mutations at the above sites, the inventor found that when these sites are mutated into different amino acids and tested for changes in the transaminase activity thereof, and found that when these amino acid sites are mutated into arbitrary one or a combination of the following, the activity and/or the stability of the transaminase is further improved The mutation includes arbitrary one or more of the followings: P243E, F89Y/W, K193E, V234I, I262V, Q280K, V379L/M/T, R416A/C/H/Q/T/S, A417S and C418A/Q/S, herein, "/" means "or".

The inventor performed a multi-point combination mutation on the above sites which have a positive effect to the catalytic activity and/or the stability, and obtained an ω-transaminase mutant with further improved catalytic properties through a directed screening method, compared with the wild-type ω-transaminase, the catalytic activity and/or the stability of the mutant is remarkably improved.

In a more preferable embodiment, the above mutation includes arbitrary one of the following combinations: V379L/M/T+F89Y/W, V379L/M/T+R416A/C/H/Q/T/S, V379L/M/T+A417S, V379L/M/T+C418A/Q/S, V379L/M/

T+P243E, V379L/M/T+K193E, V379L/M/T+V234I, V379L/M/T+I262V, V379L/M/T+Q280K, R416A/C/H/Q/T/S+A417S, R416A/C/H/Q/T/S+C418A/Q/S, R416A/C/H/Q/T/S+F89Y/W, R416A/C/H/Q/T/S+A417S+F89Y/W, V379L/M/T+R416A/C/H/Q/T/S+F89Y/W, V379L/M/T+R416A/C/H/Q/T/S+A417S, V379L/M/T+R416A/C/H/Q/T/S+C418A/Q/S, V379L/M/T+R416A/C/H/Q/T/S+K193E, V379L/M/T+R416A/C/H/Q/T/S+V234I, V379L/M/T+C418A/Q/S+F89Y/W, V379L/M/T+C418A/Q/S+P243E, V379L/M/T+C418A/Q/S+I262V, V379L/M/T+A417S+Q280K, V379L/M/T+R416A/C/H/Q/T/S+C418A/Q/S+F89Y/W, V379L/M/T+R416A/C/H/Q/T/S+C418A/Q/S+Q280K, V379L/M/T+R416A/C/H/Q/T/S+C418A/Q/S+F89Y/W+Q280K, V379L/M/T+R416A/C/H/Q/T/S+C418A/Q/S+F89Y/W+Q280K+I262V, V379L/M/T+R416A/C/H/Q/T/S+C418A/Q/S+F89Y/W+Q280K+A417S and V379L/M/T+R416A/C/H/Q/T/S+C418A/Q/S+F89Y/W+Q280K+I262V+V234I, but not limited to this.

A specific screening process of the above mutant and the combinations thereof is as follows:

36 pairs of site-directed mutagenesis primers are used for performing the site-directed mutagenesis on 36 sites (F22V, F22A, F22L, L59V, L59A, W60F, C61S, C61A, F88V, F89W, F89Y, Y153F, Y153M, Y153V, A231G, R416K, R416C, R416A, A417H, C418Q, F320V, P94E, S101K, P243E, Q280K, Q346S, P354A, F397A, W60L, T87A, V234M, V234I, I262V, T321A, V379L, V379M). 9 saturation mutation primers are used for performing the saturation mutation on 9 sites (W60, T321, V379, F89, Y153, A231, Y322, R416, A417 and C418), herein the site-directed mutagenesis primers uses primer sequences obtained by a Quick Change Primer Design website design for this experiment, sequences of the saturation mutation primers are as shown in Table 1 below. A complete linear fragment is obtained by a full vector PCR. The PCR product is digested with Dpn I so as to remove a female parent template of a starting gene, and then transformed into *Escherichia coli* BL21 (DE3), spread in an LB culture dish containing 50 μg/ml of ampicillin, and cultured overnight in 37 DEG C. The site-directed mutagenesis uses gene sequencing to determine the mutation sites, and the saturation mutation is screened by high throughput screening, and then determines the mutation sites by the gene sequencing.

TABLE 1 saturation mutation primers:

| SEQ ID NO: | Primer name | Primer sequence |
|---|---|---|
| 2 | F89-S | ccgttctacaatccttcNNKaaaaccacccacccagctg |
| 3 | F89-A | cagctgggtgggtggttttMNNgaaggtattgtagaacgg |
| 4 | Y153-S | gattggccgttggaacggcNNKcacggcagcactattggtgg |
| 5 | Y153-A | ccaccaatagtgctgccgtgMNNgccgttccaacggccaatc |
| 6 | A231-S | ggtgagccgatccagggtNNKggtggtgttatcgttccgc |
| 7 | A231-A | gcggaacgataacaccaccMNNaccctggatcggctcacc |
| 8 | Y322-S | cttcaaccacggttttaccNNKtctggtcacccagtctgcg |

TABLE 1-continued saturation mutation primers:

| SEQ ID NO: | Primer name | Primer sequence |
|---|---|---|
| 9 | Y322-A | cgcagactgggtgaccagaMNNggtaaaaccgtggttgaag |
| 10 | R416-S | ccgtaacaacctgattatgNNKgcctgcggcgatcacatcgtg |
| 11 | R416-A | cacgatgtgatcgccgcaggcMNNcataatcaggttgttacgg |
| 12 | A417-S | gtaacaacctgattatgcgtNNKtgcggcgatcacatcgtgtctg |
| 13 | A417-A | cagacacgatgtgatcgccgcaMNNacgcataatcaggttgttac |
| 14 | C418-S | caacctgattatgcgtgccNNKggcgatcacatcgtgtctgc |
| 15 | C418-A | gcagacacgatgtgatcgccMNNggcacgcataatcaggttg |
| 16 | W60-R | ccgtaaccaacgttaacacaMNNcaggccagccataccgtcaa |
| 17 | W60-F | ttgacggtatggctggcctgNNKtgtgttaacgttggttacgg |
| 18 | T321-R | cagactgggtgaccagaataMNNaaaaccgtggttgaagtcacc |
| 19 | T321-F | ggtgacttcaaccacggttttNNKtattctggtcacccagtctg |
| 20 | V379-R | ccagcgtgaacgcctgMNNcataccaacaccgcgc |
| 21 | V379-F | gcgcggtgttggtatgNNKcaggcgttcacgctgg |

(I) High Throughput Screening is Performed Using the Following Method:

1. Induction of expression in 96-well plate: a monoclone is selected and inoculated in an LB liquid culture medium containing 100 μg/ml of ampicillin, and shake-cultured at 37 DEG C. until $OD_{600}$=0.6, IPTG is added until final concentration of 0.2 mM, and induced expression is performed overnight in 25 DEG C.

2. Enzyme solution preparation method: a supernatant culture medium is removed by centrifugation of the 96-well plate, 200 μl of enzymolysis solution (2 mg/mL of lysozyme, 1 mg/mL of polymyxin, and pH=7.0) is added to each well, and incubated at 37 DEG C. and breaking is performed for 2 h. Cell breaking solution after enzymolysis is centrifuged at 4000 rpm for 10 min, and the supernatant is taken to obtain crude enzyme solution.

3. According to the system as shown in Table 2, the activity preliminary screening is performed by a microplate reader.

TABLE 2

| System | Addition amount |
|---|---|
| N-Cbz-pyrrolidone (9.26 mg/ml DMSO) | 48 μl |
| P-nitrophenylethylamine (8.11 mg/ml) | 36 μl |
| PLP (0.2 mg/ml) | 12 μl |
| Phosphate buffer solution pH 7.0 | 48 μl |
| Enzyme solution | 96 μl |

According to the system as shown in the above Table 2, other components except the enzyme solution are uniformly mixed in the 96-shallow-well plate, background detection is performed in 430 nm, and 96 µL of the prepared mutant enzyme solution is respectively added to each well, and the mixed system is immediately placed in 40 DEG C., a shaker reaction is performed in 200 rpm, after 30-40 min, an absorbance change of $OD_{430}$ is detected with the microplate reader.

Enzyme activity calculation formula: enzyme activity $(u/mL)=(\Delta A \times 60 \times V_1)/(6.22 \times t \times V_2)$.

ΔA: an absorbance value variable quantity in a reaction process;
$V_1$: a total volume of a reaction system;
6.22: an extinction coefficient;
t: detection time of ΔA; and
$V_2$: a volume of added enzyme solution.

Through comparing with the enzyme activity of the wild-type transaminase, a mutant strain with higher activity is screened, and rescreening and gene sequencing are performed.

(II) Rescreening of Transaminase Mutants:

The above preliminary-screened mutant of which the enzyme activity is higher than that of the wild-type transaminase is inoculated in 500 ml of the LB liquid culture medium containing 100 µg/ml of the ampicillin, and shake-cultured at 37 DEG C. until $OD_{600}$=0.6, the IPTG is added until the final concentration is 0.2 mM, the induced expression is performed at 25 DEG C. After induction is performed for 16 h, cells are collected by centrifuging at 6000 g for 10 min. The cells are disrupted with an ultrasonic disrupter (JY92-2D, Ningbo Xinzhi Biotechnology Co., Ltd.), and supernatant is obtained by centrifuging in 4 DEG C. and 10000 g for 20 min, and used for activity detection.

(1) N-Cbz-3-pyrrolidone is used as a substrate for detecting reaction activity of the transaminase mutant. The following system is used:

0.2 g of the N-Cbz-3-pyrrolidone substrate is dissolved in 0.5 ml of DMSO and mixed uniformly, 1.25 ml of 4.3 M of isopropylamine hydrochloride, 0.2 ml of 0.01 g/ml of PLP and 0.3-3 wt of a recombinant crude enzyme are added, the reaction system is supplemented to 20-30 V with 100 mM of the phosphate buffer solution with pH 7.0, then the pH is adjusted to 7.0, and reaction is performed at 200 rpm in a constant temperature shaker at 30 DEG C. 200 µL of the system is taken at 3 h and 16 h, 400 µL of methanol is added for uniformly mixing, centrifugation is performed at 12000 rpm for 3 minutes, 200 µL of supernatant is taken and 800 µL of the methanol is added for uniformly mixing, it is sent to a HPLC for detecting a transformation rate. The mutant with the improved catalytic activity is determined.

Partial detection results are as shown in Table 3.

TABLE 3

| Transaminase | Feeding quantity | Enzyme amount | Reaction system | Transformation rate | ee value | Time |
|---|---|---|---|---|---|---|
| Wild-type | 0.2 g | 3 wt | 30 V | 95.70% | 99% | 16 h |
| | 0.2 g | 2 wt | 30 V | 82.32% | 99% | 3 h |
| | | | | 84.31% | 99% | 6 h |
| | | | | 86.52% | 99% | 16 h |
| F89Y | 0.2 g | 1 wt | 30 V | 95.14% | 99% | 3 h |
| | | | | 96.11% | 99% | 16 h |
| R416C | 0.2 g | 1 wt | 20 v | 95.61% | 99% | 3 h |
| | | | | 96.05% | 99% | 16 h |
| R416Q | 0.2 g | 1 wt | 20 v | 87.38% | 99% | 3 h |
| | | | | 95.81% | 99% | 16 h |
| R416S | 0.2 g | 1 wt | 20 v | 96.20% | 99% | 16 h |
| C418A | 0.2 g | 1 wt | 20 v | 94.08% | 99% | 3 h |
| | | | | 95.96% | 99% | 16 h |
| V379T | 0.2 g | 1 wt | 20 v | 95.53% | 99% | 3 h |
| | | | | 96.53% | 99% | 16 h |
| V379M | 0.2 g | 1 wt | 20 V | 95.12% | 99% | 3 h |
| | | | | 97.00% | 99% | 16 h |
| V379T + C418S | 0.2 g | 0.5 wt | 20 v | 83.10% | 99% | 16 h |
| V379T + R416A | 0.2 g | 0.5 wt | 20 v | 94.98% | 99% | 16 h |
| V379T + I262V | 0.2 g | 1 wt | 20 v | 93.56% | 99% | 16 h |
| V379T + R416A + C418S + F89Y | 0.2 g | 1 wt | 20 v | 97.06% | 99% | 16 h |
| V379T + C418S + F89Y | 0.2 g | 0.5 wt | 20 v | 95.34% | 99% | 16 h |

It may be observed from Table 3 that a reaction speed of the transaminase is rapider, the transformation effects in 3 h and overnight 16 h are basically the same, and a difference between the transformation rates does not exceed 10%, however, in order to facilitate sampling operation, an overnight reaction is used in the subsequent experiments. According to some ω-transaminase mutants in the disclosure, in synthesis of a (S)-1-benzyloxycarbonyl-3-aminoheterocycle compound (especially (S)-1-benzyloxycarbonyl-3-aminopyrrolidine), the amount of enzyme is further reduced to 0.3-0.5 wt, the reaction volume is 20 V, and ee value of the obtained (S)-1-benzyloxycarbonyl-3-aminopyrrolidine is greater than 99%, so an utilization rate of the enzyme is greatly improved, and industrial production cost of the compound is greatly reduced.

In addition, reaction conditions used for synthesizing (S)-1-benzyloxycarbonyl-3-aminopiperidine and partial reaction results are shown in Table 4.

TABLE 4

| Transaminase | Feeding quantity | Enzyme amount | Reaction system | Transformation rate | ee value | Time |
|---|---|---|---|---|---|---|
| Wild-type | 0.2 g | 3 wt | 10 V | 98.00% | 98.05% | 16 h |
|  |  | 1 wt | 16 V | 93.28% | 98.00% | 16 h |
|  |  | 0.5 wt | 10 V | 68.19% | 98.16% | 16 h |
| C418A | 0.2 g | 1 wt | 11.3 V | 98.00% | 98.25% | 16 h |
|  |  | 0.5 wt | 10 V | 76.08% | 98.03% | 16 h |
| R416T | 0.2 g | 0.5 wt | 10 V | 98.26% | 98.56% | 16 h |
| R416A + C418A | 0.2 g | 0.5 wt | 10 V | 97.98% | 98.45% | 16 h |

It may be observed from Table 4 that according to some ω-transaminase mutants in the disclosure, in synthesis of the (S)-1-benzyloxycarbonyl-3-aminopiperidine, the amount of the enzyme is reduced to 0.5 wt, the reaction volume is reduced to 10 V, the transformation rate is improved by 8%-30%, the ee value is greater than 98%. A utilization ratio of the enzyme and a reaction kettle is greatly improved, production batches of enzyme solution and a usage amount of a material are effectively reduced, and the production cost is reduced.

(2) The N-Cbz-3-pyrrolidone is used as a substrate for detecting tolerance of the transaminase mutants. The following system is used:

0.2 g of the N-Cbz-3-pyrrolidone substrate is dissolved in 0.5 ml of DMSO and mixed uniformly, 1.25 ml of 4.3 M of isopropylamine hydrochloride, 0.2 ml of 0.01 g/ml of PLP, and 0.5-2 wt of the recombinant crude enzyme which is treated by 50% of DMSO at 30 DEG C. and pH 9.5 for 1 h are added, the reaction system is supplemented to 20-30 V with 100 mM of NaHCO$_3$, the pH is adjusted to 7.0, reaction is performed at 200 rpm in a constant temperature shaker at 30 DEG C. 200 μL of the system is taken at 16 h, 400 μL of the methanol is added and mixed uniformly, the centrifugation is performed at 12000 rpm for 3 minutes, 200 μL of the supernatant is taken and 800 μL of the methanol is added and mixed uniformly, it is sent to the HPLC for detecting the transformation rate. The mutant with the improved stability is determined. The partial results are as shown in Table 5.

TABLE 5

| Transaminase | Enzyme solution treatment condition | Relative residual activity |
|---|---|---|
| Wild-type | 30° C., pH 9.5, 50% DMSO treating for 1 h | 21.84% |
| V379T + R416A | 30° C., pH 9.5, 50% DMSO treating for 1 h | 62.14% |
| V379T + R416A + C418A | 30° C., pH 9.5, 50% DMSO treating for 1 h | 27.13% |
| V379T + R416A + C418S | 30° C., pH 9.5, 50% DMSO treating for 1 h | 58.05% |

The enzyme may lose the activity under extreme conditions, such as a high temperature, a strong acid, a strong alkali and an organic solvent, for a long time. Residual enzyme activity is total activity of the enzyme which still maintains the activity under the environments of the high temperature, the strong acid, the strong alkali or the organic solvent and the like. Relative residual activity refers to a percentage of the measured enzyme activity of the enzyme solution treated under the extreme conditions of the high temperature, the alkalinity, the organic solvent and the like, and the enzyme activity of the enzyme solution in the optimal conditions without being treated under the extreme environments. In a same treatment condition, the relative residual activity is high, it is indicated that the enzyme is more stable in the condition.

It may be observed from Table 5 that in the same extreme conditions, the relative residual activity of the mutant is two to three times higher than that of the wild-type transaminase. Therefore, the stability of the ω-transaminase mutant obtained in the disclosure is greatly improved, which creates better preconditions for subsequent immobilization and continuous flow reaction.

In conclusion, the catalytic activity and/or the stability of the ω-transaminase mutant obtained by the disclosure through the directed screening method is greatly improved, so the enzyme amount thereof in the transamination reaction is reduced, and the reaction system is reduced, especially the cheap isopropylamine is used as the amino donor for catalyzing a reaction of synthesizing the (S)-1-benzyloxycarbonyl-3-aminopiperidine and the (S)-1-benzyloxycarbonyl-3-aminopyrrolidine.

In a second typical implementation mode of the disclosure, a DNA molecule is provided, the DNA molecule encodes any one of the above ω-transaminase mutants. The coded transaminase mutant has an advantage of remarkably improved catalytic activity and/or stability.

In a third typical implementation mode of the disclosure, a recombinant vector is provided, the recombinant vector is linked with the above DNA molecule.

In the above recombinant vector, any recombinant vector capable of expressing a DNA molecule of the transaminase mutant is suitable for use in the present disclosure. In the preferable embodiments of the disclosure, the recombinant vector is selected from the followings: pET-21b(+), pET-22b(+), pET-3a(+), pET-3d(+), pET-11a(+), pET-12a(+), pET-14b(+), pET-15b(+), pET-16b(+), pET-17b(+), pET-19b(+), pET-20b(+), pET-21a(+), pET-23a(+), pET-23b(+), pET-24a(+), pET-25b(+), pET-26b(+), pET-27b(+), pET-28a(+), pET-29a(+), pET-30a(+), pET-31b(+), pET-32a(+), pET-35b(+), pET-38b(+), pET-39b(+), pET-40b(+), pET-41a(+), pET-41b(+), pET-42a(+), pET-43a(+), pET-43b(+), pET-44a(+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19.

In a fourth typical implementation mode of the disclosure, a host cell is provided. The host cell contains any one of the above recombinant vectors. The specific host cell is a prokaryotic cell or a eukaryocyte cell; preferably, preferably the prokaryotic cell is a yeast cell. More preferably, the above host cell is a competent cell, further preferably, the competent cell is an *Escherichia coli* BL21 cell or an *Escherichia coli* W3110.

In a fifth typical implementation mode of the disclosure, a method for producing a chiral amine is provided. The method includes a step of performing a catalytic transamination reaction on a ketones compound and an amino donor with a transaminase, herein the transaminase is any one of the above transaminase mutants.

The ketones compound is

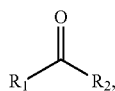

herein, each of $R_1$ and R2 is independently a C1-C8 alkyl, a C5-C10 cycloalkyl, a C6-C10 aryl or a C5-C10 heteroaryl, or the $R_1$ and the R2 jointly form a C5-C10 heterocyclyl, a C5-C10 carbocyclyl or the C5-C10 heteroaryl with carbon in a carbonyl, one or more of heteroatoms in the C5-C10 heterocyclyl and the C5-C10 heteroaryl are independently selected from at least one of nitrogen, oxygen and sulfur, and an aryl in the C6-C10 aryl, a heteroaryl in the C5-C10 heteroaryl, a carbocyclyl in the C5-C10 carbocyclyl or a heterocyclyl in the C5-C10 heterocyclyl is independently unsubstituted or substituted by at least one group of halogen, an alkoxy or an alkyl, preferably, the ketone compound is

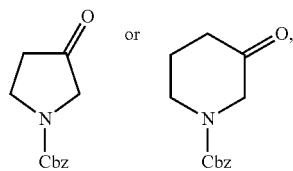 [SMILES: O=C1CCN(C(=O)OCc2ccccc2)C1 ; O=C1CCCN(C(=O)OCc2ccccc2)C1]

and a product of the transamination reaction is

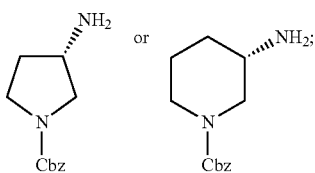 [SMILES: N[C@H]1CCN(C(=O)OCc2ccccc2)C1 ; N[C@H]1CCCN(C(=O)OCc2ccccc2)C1]

preferably, the amino donor is isopropylamine or an isopropyl amine salt.

These transaminase mutants with remarkably improved catalytic activity and/or stability may be used for greatly reducing the amount and the reaction volume of the enzyme in the synthesis of the (S)-1-benzyloxycarbonyl-3-aminoheterocycle compound, and greatly reducing the production batches and the production cost, so the enzyme has the better application value in the industrial production. The disclosure uses the cheap amino donor (such as the isopropylamine and the hydrochloride thereof) to react, and a coupling coenzyme system may not be required in the reaction. There are few types of reaction materials, and the operation is simpler.

In a process of preparing the (S)-1-benzyloxycarbonyl-3-aminoheterocycle compound, such as the (S)-1-benzyloxycarbonyl-3-aminopyrrolidine or the (S)-1-benzyloxycarbonyl-3-aminopiperidine, with the above transaminase mutant of the disclosure as a catalyst, because the catalytic activity and/or the stability of the enzyme is remarkably improved, the amount of the enzyme is apparently reduced, the reaction volume is reduced to 10-20 ml/g the substrate, and it is apparently smaller than a reaction volume in an prior art. On this basis, the above reaction temperature, time and pH value may be rationally adjusted and optimized on the basis of the present reaction conditions. When the preferable reaction conditions of the present application are used, the reaction efficiency is higher.

The disclosure is further described below through the following non-limited embodiments, it is well-known to those skilled in the art that many modifications may be made to the disclosure without departing from spirit of the disclosure, and such modifications also fall within a scope of the disclosure.

Unless otherwise specified, the following experimental methods are conventional methods, and experimental materials used may be easily obtained from commercial companies unless otherwise specified.

Embodiment 1

36 pairs of site-directed mutagenesis primers designed with a Quick Change Primer Design website and 9 saturation mutation primers as shown in Table 1 are used, a complete linear fragment is obtained by a full vector PCR, after a product of the above PCR is digested with Dpn1 so as to remove a female parent template of a starting gene, it is transformed into *Escherichia coli* BL21 (DE3), spread in an LB culture dish containing 50 μg/ml of ampicillin, and cultured overnight in 37 DEG C. Saturation mutation is screened by high throughput screening. Specifically, the above mutants are screened with the following method to perform the high throughput screening:

(1) Induction expression in 96-well plate: a monoclone is selected and inoculated in an LB liquid culture medium containing 100 μg/ml of ampicillin, and shake-cultured at 37 DEG C. until $OD_{600}$=0.6, IPTG is added until final concentration of 0.2 mM, and induced expression is performed overnight in 25 DEG C.

(2) Enzyme solution preparation method: a supernatant culture medium is removed by centrifugation of 96-well plate, 200 μl of enzymolysis solution (2 mg/mL of lysozyme, 1 mg/mL of polymyxin, and pH=7.0) is added to each well, and incubated at 37 DEG C. and breaking is performed for 2 h. Cell breaking solution after enzymolysis is centrifuged at 4000 rpm for 10 min, and the supernatant is taken to obtain crude enzyme solution.

Embodiment 2: Activity Detection to N-Cbz-3-Pyrrolidone Substrate by Transaminase Mutant The above mutant of which enzyme activity is higher than that of a wild-type transaminase is inoculated in 500 ml of the LB liquid culture medium containing 100 μg/ml of ampicillin, and shake-cultured at 37 DEG C. until $OD_{600}$=0.6, IPTG is added until final concentration of 0.2 mM, induced expression is performed at 25 DEG C. After induction is performed for 16 h, cells are collected by centrifuging at 6000 g for 10 min. The cells are disrupted with an ultrasonic disrupter (JY92-2D, Ningbo Xinzhi Biotechnology Co., Ltd.), and supernatant is obtained by centrifuging in 4 DEG C. and 10000 g for 20 min, and used for activity detection.

0.2 g of a N-Cbz-3-pyrrolidone substrate is dissolved in 0.5 ml of DMSO and mixed uniformly, 1.25 ml of 4.3 M of an isopropylamine hydrochloride, 0.2 ml of 0.01 g/ml of a PLP and 0.3-2 wt of a recombinant crude enzyme are added, a reaction system is supplemented to 20-30 V with 100 mM of phosphate buffer solution with pH 7.0, the pH is adjusted to 7.0, and reaction is performed overnight at 200 rpm in a constant temperature shaker at 30 DEG C. 200 μL of the system is taken at 16 h, 400 μL of methanol is added for uniformly mixing, centrifugation is performed at 12000 rpm for 3 minutes, supernatant is sent to a HPLC for detecting a transformation rate. The mutant with improved catalytic activity is determined.

Results of the mutant with improved catalytic activity are as shown in Table 6.

TABLE 6

| Mutant number | Mutant amino acid | Activity |
|---|---|---|
| 1 | N/A | 1 |
| 2 | F89W | + |
| 3 | F89Y | + |
| 4 | P243E | + |
| 5 | K193E | + |
| 6 | V234I | ++ |
| 7 | I262V | ++ |
| 8 | Q280K | + |
| 9 | V379L | + |
| 10 | V379M | ++ |
| 11 | V379T | ++ |
| 12 | R416A | ++ |
| 13 | R416C | ++ |
| 14 | R416H | ++ |
| 15 | R416Q | ++ |
| 16 | R416T | ++ |
| 17 | R416S | ++ |
| 18 | A417S | + |
| 19 | C418A | ++ |
| 20 | C418Q | ++ |
| 21 | C418S | ++ |
| 22 | V379L + F89W | ++ |
| 23 | V379T + F89Y | +++ |
| 24 | V379M + R416A | +++ |
| 25 | V379M + R416C | ++ |
| 26 | R416T + F89Y | +++ |
| 27 | V379T + R416S | +++ |
| 28 | R416A + A417S | +++ |
| 29 | V379M + A417S | ++ |
| 30 | V379T + C418A | ++ |
| 31 | V379T + C418Q | ++ |
| 32 | V379T + C418S | ++ |
| 33 | V379M + P243E | ++ |
| 34 | V379M + K193E | ++ |
| 35 | V379T + V234I | +++ |
| 36 | V379T + I262V | ++ |
| 37 | V379T + Q280K | ++ |
| 38 | V379T + R416H | +++ |
| 39 | R416A + C418A | ++++ |
| 40 | R416A + C418S | +++ |
| 41 | V379T + R416A | +++ |

TABLE 6-continued

| Mutant number | Mutant amino acid | Activity |
|---|---|---|
| 42 | V379T + R416A + C418S | ++++ |
| 43 | V379T + R416A + C418A | +++ |
| 44 | V379T + R416S + F89W | +++ |
| 45 | V379T + R416T + A417S | +++ |
| 46 | V379T + R416A + F89Y | +++ |
| 47 | R416T + A417S + F89Y | ++ |
| 48 | V379T + R416T + K193E | +++ |
| 49 | V379T + R416S + V234I | ++++ |
| 50 | V379T + C418S + F89Y | +++ |
| 51 | V379T + C418A + P243E | +++ |
| 52 | V379T + C418Q + I262V | +++ |
| 53 | V37T + A417S + Q280K | +++ |
| 54 | V379T + R416A + C418S + F89Y | ++ |
| 55 | V379T + R416A + C418A + F89Y | ++++ |
| 56 | V379T + R416T + C418A + Q280K | +++ |
| 57 | V379T + R416A + C418A + F89Y + Q280K | +++ |
| 58 | V379T + R416A + C418Q + F89Y + Q280K + I262V | +++ |
| 59 | V379T + R416A + C418A + F89Y + Q280K + A417S | +++ |
| 60 | V379T + R416T + C418A + F89Y + Q280K + I262V + V234I | ++++ |

"1" means 3 wt of a ketoreductase crude enzyme, while a reaction system is 30 V, a transformation rate in 16 h is greater than 93%; "+" means 1 wt of the ketoreductase crude enzyme, while the reaction system is 30 V, the transformation rate in 16 h is greater than 93%; "++" means 1 wt of the ketoreductase crude enzyme, while the reaction system is 20 V, the transformation rate in 16 h is greater than 93%; "+++" means 0.5 wt of the ketoreductase crude enzyme, while the reaction system is 20 V, the transformation rate in 16 h is greater than 93%; and "++++" means 0.3-0.5 wt of the ketoreductase crude enzyme, while the reaction system is 20 V, the transformation rate in 16 h is 94%-100%.

Embodiment 3

33 induction-expressed transaminases mutants numbered 1 to 21, 33 to 43 and 54 are used for screening synthesis reactions of (S)-1-benzyloxycarbonyl-3-aminopiperidine, and the following reaction system is used: 0.2 g of a N-BOC-3-piperidone substrate is dissolved in 0.3 ml of DMSO and mixed uniformly, 698 ul of 4.3 M of isopropylamine hydrochloride, 2 mg of PLP, and 0.5-3 wt of a recombinant crude enzyme are added, a reaction system is supplemented to 10-16 V with 100 mM of phosphate buffer solution in pH 7.0, the pH is adjusted to 7.0, and reaction is performed overnight at 200 rpm, 30 DEG C. Through reaction screening, reaction results of strains with relatively better activity are as shown in Table 7. Catalytic activity of 21 residual transaminase mutants except those shown in Table 7 is not increased compared to the activity of a wild-type transaminase.

TABLE 7

| Transaminase | Feeding quantity | Enzyme amount | Reaction system | Transformation rate | ee value | Time |
|---|---|---|---|---|---|---|
| Wild-type | 0.2 g | 3 wt | 10 V | 98.00% | 98.05% | 16 h |
|  |  | 1 wt | 16 V | 93.28% | 98.00% | 16 h |
|  |  | 0.5 wt | 10 V | 68.19% | 98.16% | 16 h |
| C418A | 0.2 g | 1 wt | 11.3 V | 98.00% | 98.25% | 16 h |
|  |  | 0.5 wt | 10 V | 76.08% | 98.03% | 16 h |
| R416T | 0.2 g | 0.5 wt | 10 V | 98.26% | 98.56% | 16 h |
| R416A | 0.2 g | 1 wt | 11.3 V | 97.98% | 98.00% | 16 h |
|  |  | 0.5 wt | 10 V | 81.58% | 98.15% | 16 h |
| R416Q | 0.2 g | 0.5 wt | 10 V | 73.71% | 98.71% | 16 h |
| C418E | 0.2 g | 0.5 wt | 10 V | 90.81% | 98.00% | 16 h |
| R416A + C418A | 0.2 g | 0.5 wt | 10 V | 97.98% | 98.45% | 16 h |
| V379T + R416H | 0.2 g | 0.5 wt | 10 V | 93.53% | 98.0% | 16 h |
| V379T + R416A | 0.2 g | 0.5 wt | 10 V | 93.18% | 98.2% | 16 h |
| R416A + C418S | 0.2 g | 1 wt | 11.3 V | 98.18% | 98.31% | 16 h |
|  |  | 0.5 wt | 10 V | 97.08% | 98.31% | 16 h |
| V379T + R416A + C418S | 0.2 g | 0.5 wt | 10 V | 97.08% | 98.1% | 16 h |

TABLE 7-continued

| Transaminase | Feeding quantity | Enzyme amount | Reaction system | Transformation rate | ee value | Time |
|---|---|---|---|---|---|---|
| V379T + R416A + C418A | 0.2 g | 1 wt | 11.3 V | 98.20% | 98.25% | 16 h |
|  |  | 0.5 wt | 10 V | 95.27% | 98.61% | 16 h |
| V379T + R416A + C418S + F89Y | 0.2 g | 0.5 wt | 10 V | 98.3% | 99% | 16 h |

Embodiment 4: N-Cbz-3-Pyrrolidone is Used as a Substrate for Detecting Tolerance of Transaminase Mutants 0.5 wt of a transaminase crude enzyme, after treated by 50% of DMSO in 30 DEG C. and pH 9.5 for 1 h, is used for the following reaction: 0.2 g of the N-Cbz-3-piperidone substrate is dissolved in 0.3 ml of the DMSO and mixed uniformly, 698 ul of 4.3 M of isopropylamine hydrochloride, and 0.2 ml of 0.01 g/ml of PLP are added, a reaction system is supplemented to 11 V with 100 mM of $NaHCO_3$, the pH is adjusted to 9.5, reaction is performed overnight at 200 rpm on a constant temperature shaker at 30 DEG C. 200 μL of the system is taken at 16 h, 400 μL of the methanol is added and mixed uniformly, centrifugation is performed in 12000 rpm for 3 minutes, supernatant is sent to a HPLC for detecting a transformation rate. Specific results are as shown in Table 8.

TABLE 8

| Transaminase | Relative residual activity |
|---|---|
| Wild-type | 18.13% |
| V379T + R416A | 33.96% |
| V379T + R416H | 27.91% |
| V379T + R416A + C418A | 26.09% |
| R416T | 40.25% |
| V379T + R416A + C418S + F89Y | 50.7% |

It may be observed from Table 8 that in a same treatment condition, stability of some transaminase mutants is higher compared to the wild-type transaminase.

Embodiment 5

4 transaminase crude enzymes in 0.5 wt, after treated by 50%-60% of DMSO in 30 DEG C. and pH 9.5 for 1 h, are used for the following reaction: 0.2 g of a N-Cbz-3-piperidone substrate is dissolved in 0.3 ml of DMSO and mixed uniformly, 698 ul of 4.3 M of isopropylamine hydrochloride, and 0.2 ml of 0.01 g/ml of PLP are added, a reaction system is supplemented to 2 ml with 100 mM of $NaHCO_3$, the pH is adjusted to 9.5, and reaction is performed overnight at 200 rpm on a constant temperature shaker at 30 DEG C. 200 μL of the system is taken at 16 h, 400 μL of the methanol is added and mixed uniformly, centrifugation is performed in 12000 rpm for 3 minutes, supernatant is sent to a HPLC for detecting a transformation rate. Results are as shown in Table 9.

TABLE 9

| Transaminase | Enzyme solution treatment condition | Relative residual activity |
|---|---|---|
| Wild-type | 30° C., pH 9.5, 50% DMSO treating for 1 h | 12.36% |
|  | 30° C., pH 9.5, 60% DMSO treating for 1 h | 0 |
| V379T + R416A | 30° C., pH 9.5, 50% DMSO treating for 1 h | 30.87% |
| V379T + R416A + C418A | 30° C., pH 9.5, 50% DMSO treating for 1 h | 24.65% |
| V379T + R416H | 30° C., pH 9.5, 50% DMSO treating for 1 h | 26.1% |
| V379T + R416A + C418S + F89Y | 30° C., pH 9.5, 50% DMSO treating for 1 h | 49.9% |
|  | 30° C., pH 9.5, 60% DMSO treating for 1 h | 18.1% |

Embodiment 6: Application of Transaminase Mutant in Synthesis of Preparing (S)-1-Benzyloxycarbonyl-3-Aminopyrrolidine A reaction equation thereof is as follows:

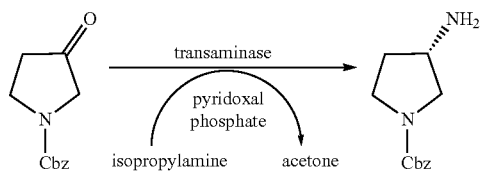 [SMILES: O=C1CCN(C(=O)OCc2ccccc2)C1 ; N[C@H]1CCN(C(=O)OCc2ccccc2)C1]

A reaction system is as follows: 1 g of a N-Cbz-3-pyrrolidone substrate is dissolved in 2.5 ml of DMSO and mixed uniformly, 6.25 ml of 4.3 M of isopropylamine hydrochloride, 1 ml of 0.01 g/ml of PLP (pyridoxal phosphate), and 0.3-0.5 wt of a V379T+R416A+C418A+F89Y recombinant crude enzyme are added, the reaction system is supplemented to 20 V with 100 mM of phosphate buffer solution in pH 7.0, the pH is adjusted to 7.0, and reaction is performed overnight at 200 rpm on a constant temperature shaker at 30 DEG C. Detection is performed by HPLC, a transformation rate in 16 h is 96.38%, after the reaction is finished, the system is adjusted to be alkalinity, methyl tert-ether is added for extracting for 3 times, after extracted organic phases are merged, a magnesium sulfate is added for drying, rotary evaporation is performed until it is dried, a yield is 80-86%, and a ee value is greater than 99%.

Embodiment 7: Application of Transaminase Mutant in Synthesis of Preparing (S)-1-benzyloxycarbonyl-3-aminopiperidine A reaction equation thereof is as follows:

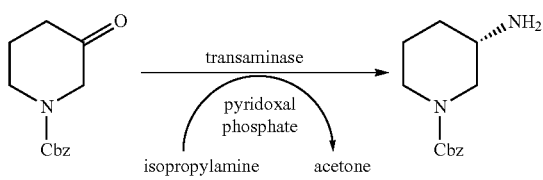

A reaction system is as follows: 2 g of a N-BOC-3-piperidone substrate is dissolved in 3 ml of DMSO and mixed uniformly, 6.98 ml of 4.3 M of isopropylamine hydrochloride, 20 mg of PLP (pyridoxal phosphate), and 0.5 wt of a V379T+R416A+C418S+F89Y recombinant crude enzyme are added, the reaction system is supplemented to 10 V with 100 mM of phosphate buffer solution in pH 7.0, the pH is adjusted to 7.0, and reaction is performed overnight at 200 rpm on constant temperature shaker at 30 DEG C. Detection is performed by HPLC, a transformation rate in 16 h is 98.3%, after the reaction is finished, the system is adjusted to be alkalinity, methyl tert-ether is added for extracting for 3 times, after extracted organic phases are merged, a magnesium sulfate is added for drying, rotary evaporation is performed until it is dried, a yield is 90%, and a ee value is greater than 99%.

It may be observed from the above description that the above embodiments of the disclosure achieve the following technical effects:

Based on partial ω-transaminase mutants obtained by the present application, in synthesis of a (S)-1-benzyloxycarbonyl-3-aminoheterocycle compound (especially (S)-1-benzyloxycarbonyl-3-aminopyrrolidine and (S)-1-benzyloxycarbonyl-3-aminopiperidine), an amount of the enzyme is reduced to 0.3-0.5 wt, a reaction volume is reduced to 10-20 V, a utilization ratio of the enzyme and a utilization ratio of a reaction kettle are greatly improved, the production batches of the enzyme solution and a usage amount of a material are reduced, and a usage amount of the organic solvent in the post-treatment is effectively reduced, so the difficulty of the post-treatment and a discharge amount of three wastes are reduced, and the labor cost is reduced. In addition, through the obtained (S)-1-benzyloxycarbonyl-3-aminopyrrolidine and (S)-1-benzyloxycarbonyl-3-aminopiperidine with high optical purity, the industrial production cost of the compound is greatly reduced, and the enzyme has a better application value in industrial production.

The above are merely the preferable embodiments of the disclosure, and not intended to limit the disclosure. Various modifications and changes may be made to the disclosure by those skilled in the art. Any modifications, equivalent replacements, improvements and the like made within spirit and principles of the disclosure shall be included in a scope of protection of the disclosure.

---

What is claimed is:

1. A transaminase mutant, wherein the amino acid sequence of the transaminase mutant is the mutated amino acid sequence of SEQ ID NO: 1, and wherein the mutated amino acid sequence comprises mutations at one or more of amino acids selected from a group consisting of P243E, F89Y/W, K193E, V234I, I262V, Q280K, V379L/M/T, R416A/C/H/Q/T/S, A417S and C418A/Q/S, wherein "/" stands for "or", and wherein the mutations at one or more of amino acids must comprise V379.

2. The transaminase mutant according to claim 1, wherein the mutations at one or more amino acids comprise any one of the following combinations:
V379L/M/T+F89Y/W, V379L/M/T+R416A/C/H/Q/T/S, V379L/M/T+A417S, V379L/M/T+C418A/Q/S, V379L/M/T+P243E, V379L/M/T+K193E, V379L/M/T+V234I, V379L/M/T+I262V, V379L/M/T+Q280K, V379L/M/T+R416A/C/H/Q/T/S+F89Y/W, V379L/M/T+R416A/C/H/Q/T/S+A417S, V379L/M/T+R416A/C/H/Q/T/S+C418A/Q/S, V379L/M/T+R416A/C/H/Q/T/S+K193E, V379L/M/T+R416A/C/H/Q/T/S+V234I, V379L/M/T+C418A/Q/S+F89Y/W, V379L/M/T+C418A/Q/S+P243E, V379L/M/T+C418A/Q/S+I262V, V379L/M/T+A417S+Q280K, V379L/M/T+R416A/C/H/Q/T/S+C418A/Q/S+F89Y/W, V379L/M/T+R416A/C/H/Q/T/S+C418A/Q/S+Q280K, V379L/M/T+R416A/C/H/Q/T/S+C418A/Q/S+F89Y/W+Q280K, V379L/M/T+R416A/C/H/Q/T/S+C418A/Q/S+F89Y/W+Q280K+I262V, V379L/M/T+R416A/C/H/Q/T/S+C418A/Q/S+F89Y/W+Q280K+A417S and V379L/M/T+R416A/C/H/Q/T/S+C418A/Q/S+F89Y/W+Q280K+I262V+V234I.

3. A method for synthesizing a chiral amine, comprising a step of performing a catalytic transamination reaction on a ketone compound and an amino donor with a transaminase, wherein the transaminase is the transaminase mutant according to claim 1.

4. The method according to claim 3, wherein the ketone compound is

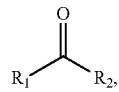

wherein each of $R_1$ and $R_2$ is independently a C1~C8 alkyl, a C5~C10 cycloalkyl, a C6~C10 aryl or a C5~C10 heteroaryl; or the $R_1$ and $R_2$ jointly form a C5~C10 heterocyclyl, a C5~C10 carbocyclyl or the C5~C10 heteroaryl with a carbon in a carbonyl; one or more of heteroatoms in the C5~C10 heterocyclyl and the C5~C10 heteroaryl are independently selected from a group consisting of nitrogen, oxygen and sulfur; an aryl in the C6~C10 aryl, a heteroaryl in the C5~C10 heteroaryl, a carbocyclyl in the C5~C10 carbocyclyl or a heterocyclyl in the C5~C10 heterocyclyl is independently unsubstituted or substituted by at least one group of halogen, an alkoxy and an alkyl.

5. The method according to claim 3, wherein the ketone compound is

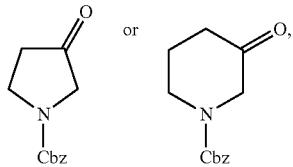 [SMILES: O=C1CCN(C(=O)OCc2ccccc2)C1 ; O=C1CCCN(C(=O)OCc2ccccc2)C1]

and a product of the transamination reaction is
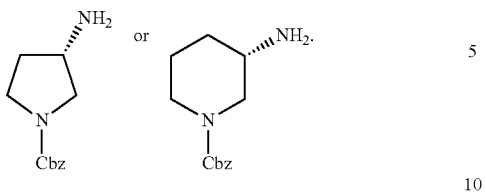
6. The method according to claim 3, wherein the amino donor is isopropyl amine or an isopropyl amine salt.
* * * * *

SEQUENCE LISTING

<160> NUMBER OF SEQ ID NOS: 21

<210> SEQ ID NO 1
<211> LENGTH: 459
<212> TYPE: PRT
<213> ORGANISM: Chromobacterium violaceum

<400> SEQUENCE: 1

```
Met Gln Lys Gln Arg Thr Thr Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Ser Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
```

```
                    165                 170                 175
        Ile Pro Gly Met Ala His Ile Glu Gln Pro Trp Trp Tyr Lys His Gly
                180                 185                 190

Lys Asp Met Thr Pro Asp Glu Phe Gly Val Val Ala Ala Arg Trp Leu
                195                 200                 205

Glu Glu Lys Ile Leu Glu Ile Gly Ala Asp Lys Val Ala Ala Phe Val
                210                 215                 220

Gly Glu Pro Ile Gln Gly Ala Gly Gly Val Ile Val Pro Pro Ala Thr
        225                 230                 235                 240

Tyr Trp Pro Glu Ile Glu Arg Ile Cys Arg Lys Tyr Asp Val Leu Leu
                        245                 250                 255

Val Ala Asp Glu Val Ile Cys Gly Phe Gly Arg Thr Gly Glu Trp Phe
                260                 265                 270

Gly His Gln His Phe Gly Phe Gln Pro Asp Leu Phe Thr Ala Ala Lys
                275                 280                 285

Gly Leu Ser Ser Gly Tyr Leu Pro Ile Gly Ala Val Phe Val Gly Lys
                290                 295                 300

Arg Val Ala Glu Gly Leu Ile Ala Gly Gly Asp Phe Asn His Gly Phe
        305                 310                 315                 320

Thr Tyr Ser Gly His Pro Val Cys Ala Ala Val Ala His Ala Asn Val
                        325                 330                 335

Ala Ala Leu Arg Asp Glu Gly Ile Val Gln Arg Val Lys Asp Asp Ile
                340                 345                 350

Gly Pro Tyr Met Gln Lys Arg Trp Arg Glu Thr Phe Ser Arg Phe Glu
                355                 360                 365

His Val Asp Asp Val Arg Gly Val Gly Met Val Gln Ala Phe Thr Leu
                370                 375                 380

Val Lys Asn Lys Ala Lys Arg Glu Leu Phe Pro Asp Phe Gly Glu Ile
        385                 390                 395                 400

Gly Thr Leu Cys Arg Asp Ile Phe Phe Arg Asn Asn Leu Ile Met Arg
                        405                 410                 415

Ala Cys Gly Asp His Ile Val Ser Ala Pro Pro Leu Val Met Thr Arg
                420                 425                 430

Ala Glu Val Asp Glu Met Leu Ala Val Ala Glu Arg Cys Leu Glu Glu
                435                 440                 445

Phe Glu Gln Thr Leu Lys Ala Arg Gly Leu Ala
                450                 455

<210> SEQ ID NO 2
<211> LENGTH: 40
<212> TYPE: DNA
<213> ORGANISM: Chromobacterium violaceum
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (21)..(21)
<223> OTHER INFORMATION: k is g, or t

<400> SEQUENCE: 2
ccgttctaca ataccttcnn kaaaaccacc cacccagctg                          40

<210> SEQ ID NO 3
<211> LENGTH: 40
<212> TYPE: DNA
<213> ORGANISM: Chromobacterium violaceum
```

<220> FEATURE:
<221> NAME/KEY: misc_feature
<222> LOCATION: (20)..(20)
<223> OTHER INFORMATION: m is a or c
<220> FEATURE:
<221> NAME/KEY: misc_feature
<222> LOCATION: (21)..(22)
<223> OTHER INFORMATION: n is a,t, g or c

<400> SEQUENCE: 3
cagctgggtg ggtggttttm nngaaggtat tgtagaacgg        40

<210> SEQ ID NO 4
<211> LENGTH: 42
<212> TYPE: DNA
<213> ORGANISM: Chromobacterium violaceum
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (22)..(22)
<223> OTHER INFORMATION: k is g or t

<400> SEQUENCE: 4
gattggccgt tggaacggcn nkcacggcag cactattggt gg        42

<210> SEQ ID NO 5
<211> LENGTH: 42
<212> TYPE: DNA
<213> ORGANISM: Chromobacterium violaceum
<220> FEATURE:
<221> NAME/KEY: misc_feature
<222> LOCATION: (21)..(21)
<223> OTHER INFORMATION: m is a, or c
<220> FEATURE:
<221> NAME/KEY: misc_feature
<222> LOCATION: (22)..(23)
<223> OTHER INFORMATION: n is a, c, g, or t

<400> SEQUENCE: 5
ccaccaatag tgctgccgtg mnngccgttc aacggccaa tc      42

<210> SEQ ID NO 6
<211> LENGTH: 40
<212> TYPE: DNA
<213> ORGANISM: Chromobacterium violaceum
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (21)..(21)
<223> OTHER INFORMATION: k is g, or t

<400> SEQUENCE: 6
ggtgagccga tccagggtnn kggtggtgtt atcgttccgc        40

<210> SEQ ID NO 7
<211> LENGTH: 40
<212> TYPE: DNA
<213> ORGANISM: Chromobacterium violaceum
<220> FEATURE:
<221> NAME/KEY: misc_feature
<222> LOCATION: (20)..(20)
<223> OTHER INFORMATION: m is a, or c
<220> FEATURE:
<221> NAME/KEY: misc_feature
<222> LOCATION: (21)..(22)

<223> OTHER INFORMATION: n is a, c, g, or t

<400> SEQUENCE: 7
gcggaacgat aacaccaccm nnaccctgga tcggctcacc                                40

<210> SEQ ID NO 8
<211> LENGTH: 41
<212> TYPE: DNA
<213> ORGANISM: Chromobacterium violaceum
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (22)..(22)
<223> OTHER INFORMATION: k is a, or c

<400> SEQUENCE: 8
cttcaaccac ggttttaccn nktctggtca cccagtctgc g                              41

<210> SEQ ID NO 9
<211> LENGTH: 41
<212> TYPE: DNA
<213> ORGANISM: Chromobacterium violaceum
<220> FEATURE:
<221> NAME/KEY: misc_feature
<222> LOCATION: (20)..(20)
<223> OTHER INFORMATION: m is a,or c
<220> FEATURE:
<221> NAME/KEY: misc_feature
<222> LOCATION: (21)..(22)
<223> OTHER INFORMATION: n is a, c, g, or t

<400> SEQUENCE: 9
cgcagactgg gtgaccagam nnggtaaaac cgtggttgaa g                              41

<210> SEQ ID NO 10
<211> LENGTH: 43
<212> TYPE: DNA
<213> ORGANISM: Chromobacterium violaceum
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (22)..(22)
<223> OTHER INFORMATION: k is g, or t

<400> SEQUENCE: 10
ccgtaacaac ctgattatgn nkgcctgcgg cgatcacatc gtg                            43

<210> SEQ ID NO 11
<211> LENGTH: 43
<212> TYPE: DNA
<213> ORGANISM: Chromobacterium violaceum
<220> FEATURE:
<221> NAME/KEY: misc_feature
<222> LOCATION: (22)..(22)
<223> OTHER INFORMATION: m is a,or c
<220> FEATURE:
<221> NAME/KEY: misc_feature
<222> LOCATION: (23)..(24)
<223> OTHER INFORMATION: n is a, c, g, or t

<400> SEQUENCE: 11
cacgatgtga tcgccgcagg cmnncataat caggttgtta cgg                            43

```
<210> SEQ ID NO 12
<211> LENGTH: 45
<212> TYPE: DNA
<213> ORGANISM: Chromobacterium violaceum
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (23)..(23)
<223> OTHER INFORMATION: k is g, or t

<400> SEQUENCE: 12
gtaacaacct gattatgcgt nnktgcggcg atcacatcgt gtctg              45

<210> SEQ ID NO 13
<211> LENGTH: 45
<212> TYPE: DNA
<213> ORGANISM: Chromobacterium violaceum
<220> FEATURE:
<221> NAME/KEY: misc_feature
<222> LOCATION: (23)..(23)
<223> OTHER INFORMATION: m is a, or c
<220> FEATURE:
<221> NAME/KEY: misc_feature
<222> LOCATION: (24)..(25)
<223> OTHER INFORMATION: n is a, c, g, or t

<400> SEQUENCE: 13
cagacacgat gtgatcgccg camnnacgca taatcaggtt gttac              45

<210> SEQ ID NO 14
<211> LENGTH: 42
<212> TYPE: DNA
<213> ORGANISM: Chromobacterium violaceum
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (22)..(22)
<223> OTHER INFORMATION: k is g, or t

<400> SEQUENCE: 14
caacctgatt atgcgtgccn nkggcgatca catcgtgtct gc                 42

<210> SEQ ID NO 15
<211> LENGTH: 42
<212> TYPE: DNA
<213> ORGANISM: Chromobacterium violaceum
<220> FEATURE:
<221> NAME/KEY: misc_feature
<222> LOCATION: (21)..(21)
<223> OTHER INFORMATION: m is a,or c
<220> FEATURE:
<221> NAME/KEY: misc_feature
<222> LOCATION: (22)..(23)
<223> OTHER INFORMATION: n is a, c, g, or t

<400> SEQUENCE: 15
gcagacacga tgtgatcgcc mnnggcacgc ataatcaggt tg                 42

<210> SEQ ID NO 16
<211> LENGTH: 43
<212> TYPE: DNA
<213> ORGANISM: Chromobacterium violaceum
<220> FEATURE:
<221> NAME/KEY: misc_feature
<222> LOCATION: (21)..(21)
```

<223> OTHER INFORMATION: m is a, or c
<220> FEATURE:
<221> NAME/KEY: misc_feature
<222> LOCATION: (22)..(23)
<223> OTHER INFORMATION: n is a, c, g, or t

<400> SEQUENCE: 16
ccgtaaccaa cgttaacaca mnncaggcca gccataccgt caa         43

<210> SEQ ID NO 17
<211> LENGTH: 43
<212> TYPE: DNA
<213> ORGANISM: Chromobacterium violaceum
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, t or u
<220> FEATURE:
<221> NAME/KEY: misc_feature
<222> LOCATION: (22)..(22)
<223> OTHER INFORMATION: n is a, c, g, t or u
<220> FEATURE:
<221> NAME/KEY: misc_feature
<222> LOCATION: (23)..(23)
<223> OTHER INFORMATION: k is g, or t

<400> SEQUENCE: 17
ttgacggtat ggctggcctg nnktgtgtta acgttggtta cgg         43

<210> SEQ ID NO 18
<211> LENGTH: 44
<212> TYPE: DNA
<213> ORGANISM: Chromobacterium violaceum
<220> FEATURE:
<221> NAME/KEY: misc_feature
<222> LOCATION: (21)..(21)
<223> OTHER INFORMATION: m is a,or c
<220> FEATURE:
<221> NAME/KEY: misc_feature
<222> LOCATION: (22)..(23)
<223> OTHER INFORMATION: n is a, c, g, or t

<400> SEQUENCE: 18
cagactgggt gaccagaata mnnaaaaccg tggttgaagt cacc         44

<210> SEQ ID NO 19
<211> LENGTH: 44
<212> TYPE: DNA
<213> ORGANISM: Chromobacterium violaceum
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g, or t

<400> SEQUENCE: 19
ggtgacttca accacggttt tnnktattct ggtcacccag tctg         44

<210> SEQ ID NO 20
<211> LENGTH: 35
<212> TYPE: DNA
<213> ORGANISM: Chromobacterium violaceum
<220> FEATURE:
<221> NAME/KEY: misc_feature

```
<222> LOCATION: (17)..(17)
<223> OTHER INFORMATION: m is a,or c
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, t or u
<220> FEATURE:
<221> NAME/KEY: misc_feature
<222> LOCATION: (19)..(19)
<223> OTHER INFORMATION: n is a, c, g, t or u

<400> SEQUENCE: 20
ccagcgtgaa cgcctgmnnc ataccaacac cgcgc                             35

<210> SEQ ID NO 21
<211> LENGTH: 35
<212> TYPE: DNA
<213> ORGANISM: Chromobacterium violaceum
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (19)..(19)
<223> OTHER INFORMATION: k is g, or t

<400> SEQUENCE: 21
gcgcggtgtt ggtatgnnkc aggcgttcac gctgg                             35
```